United States Patent
Song et al.

(10) Patent No.: US 9,745,263 B2
(45) Date of Patent: Aug. 29, 2017

(54) USE OF MAGNETIC IRON OXIDE RED IN CATALYZING AND OXIDIZING METHANTHIOL AND METHODS FOR PREPARING AND APPLING SAME

(71) Applicant: BEIJING SJ ENVIRONMENTAL PROTECTION AND NEW MATERIAL CO., LTD., Beijing (CN)

(72) Inventors: Wenwen Song, Beijing (CN); Liying Li, Beijing (CN); Wenjun Mao, Beijing (CN); Zhimin Zhang, Beijing (CN); Zhenyi Liu, Beijing (CN)

(73) Assignee: BEIJING SJ ENVIROMENTAL PROTECTION AND NEW MATERIAL CO., LTD., Beijing (CN)

( * ) Notice: Subject to any disclaimer, the term of this patent is extended or adjusted under 35 U.S.C. 154(b) by 0 days.

(21) Appl. No.: 15/108,908

(22) PCT Filed: Dec. 22, 2014

(86) PCT No.: PCT/CN2014/094509
§ 371 (c)(1),
(2) Date: Jun. 29, 2016

(87) PCT Pub. No.: WO2015/101191
PCT Pub. Date: Jul. 9, 2015

(65) Prior Publication Data
US 2016/0326106 A1    Nov. 10, 2016

(30) Foreign Application Priority Data

Dec. 31, 2013  (CN) .......................... 2013 1 0751115

(51) Int. Cl.
| | | |
|---|---|---|
| C07C 319/24 | (2006.01) | |
| B01J 23/745 | (2006.01) | |
| B01J 35/00 | (2006.01) | |
| B01J 37/00 | (2006.01) | |
| C01G 49/02 | (2006.01) | |
| B01J 37/03 | (2006.01) | |
| B01J 37/08 | (2006.01) | |
| B01J 37/04 | (2006.01) | |
| B01J 37/06 | (2006.01) | |

(52) U.S. Cl.
CPC .......... *C07C 319/24* (2013.01); *B01J 23/745* (2013.01); *B01J 35/0033* (2013.01); *B01J 37/0009* (2013.01); *B01J 37/031* (2013.01); *B01J 37/04* (2013.01); *B01J 37/06* (2013.01); *B01J 37/08* (2013.01); *B01J 37/088* (2013.01); *C01G 49/02* (2013.01); *B01J 37/0018* (2013.01)

(58) Field of Classification Search
CPC ..... C07C 319/24; B01J 37/0009; B01J 37/04; B01J 37/06; B01J 37/08; B01J 35/0033; B01J 23/745
USPC .................... 568/21, 26; 502/338; 423/594.1
See application file for complete search history.

(56) References Cited

U.S. PATENT DOCUMENTS 5,304,683 A   4/1994 Sattich

FOREIGN PATENT DOCUMENTS

| CN | 102816093 A | | 12/2012 |
|---|---|---|---|
| CN | 103183389 A | * | 7/2013 |
| CN | 103183389 A | | 7/2013 |
| JP | 10174873 A | | 6/1998 |

OTHER PUBLICATIONS

Machine-generated translation of the description of CN102183389A from Patent Translate (Powered by EPO and Google), May 5, 2017.*
International Search Report for Application No. PCT/CN2014/094509, mailed Mar. 30, 2015, 4 pages.
Yaqing et al., Study on New Manufacture Technology of High Quality Red Iron Oxide from Ferrous Sulfate, Jan. 31, 2013, Inorganic Chemicals Industry, 45(1): 44-46, 4 pages.
Translated Chinese Office Action for Application No. 201310751115.X, mailed on Dec. 21, 2016, a counterpart foreign application of U.S. Appl. No. 15/108,908, 9 pages.

* cited by examiner

*Primary Examiner* — Porfirio Nazario Gonzalez
(74) *Attorney, Agent, or Firm* — Lee & Hayes, pllc

(57) ABSTRACT

The present invention relates to a novel use of magnetic iron oxide red $Fe_{21.333}O_{32}$ as a catalyst in oxidizing methanthiol to prepare dimethyl disulfide. The magnetic iron oxide red $Fe_{21.333}O_{32}$ according to the present invention has extremely high catalytic selectivity in catalyzing and oxidizing methanthiol to prepare dimethyl disulfide. The magnetic iron oxide red $Fe_{21.333}O_{32}$ is prepared with a carbonate and a ferrite as raw materials, has advantages of low cost and simple preparation process, and is suitable for industrial production.

12 Claims, 3 Drawing Sheets

USE OF MAGNETIC IRON OXIDE RED IN CATALYZING AND OXIDIZING METHANTHIOL AND METHODS FOR PREPARING AND APPLING SAME

The present application is a U.S. National Phase Application of International Application No. PCT/CN2014/094509, filed Dec. 22, 2014, which claims the benefit of Chinese Application No. 20130751115.X, filed Dec. 31, 2013, both of which are hereby incorporated by reference in their entirety.

FIELD OF THE INVENTION

The present invention relates to a technical field of catalysis, in particular to a catalyst for catalyzing and oxidizing methanthiol gas and methods for preparation and application thereof.

BACKGROUND OF THE INVENTION

Dimethyl disulfide is a widely used chemical raw material, which can be used for synthesizing methanesulfonyl chloride and methanesulfonic acid products. In addition, dimethyl disulfide is an organic solvent often used in polymerization and cyanation reactions. In the food industry, dimethyl sulfide is allowed to be used as an edible flavor. Besides, dimethyl disulfide can be used as a catalyst and passivating agent in petroleum industry, an odor agent for city gas, an industrial cleaning agent, a pesticide penetrating agent and the like. Therefore, it is a research hotspot for the skilled person in the art to study the preparation technology of dimethyl disulfide.

In theory, it is an available way for preparing dimethyl disulfide by catalytic oxidation of raw material methanthiol ($4CH_3SH + O_2 \rightarrow 2CH_3SSCH_3 + 2H_2O$). However researches of industrial production process of preparing dimethyl disulfide by catalytic oxidation of raw material methanthiol haven't been under way. Chinese patent application CN102816093A discloses a method for preparing dimethyl disulfide by oxidization of methanthiol, comprising introducing a mixture gas of methanthiol, oxygen and nitrogen dioxide with molar ratio 4:1.25:0.2 into a tower reactor to perform oxidation reaction in the presence of an emulsifying agent by controlling the molar ratio of methanthiol to emulsifying agent to 1:10-30 at a reaction temperature of 10-150° C. and a pressure of 0.01-0.1 MPa to produce a reaction product, then after 10 to 20 minutes' standing, dimethyl disulfide is separated from the reaction product. In this method a qualified dimethyl disulfide product is prepared by using nitrogen dioxide as a catalyst and by reaction, separation and rectification processes.

Although researches of industrial production process of preparing dimethyl disulfide by catalytic oxidation of raw material methanthiol haven't been under way, and there lacks of intensive study on catalyst for catalytic oxidation of methanthiol, the process of preparing dimethyl disulfide by catalytic oxidation of methanthiol still has vast development potential because it has some advantages such as simple and safe. In order to realize its industrial production, the problem to be solved in the prior art is to develop new catalysts to improve the catalytic conversion rate of methanthiol.

SUMMARY OF THE INVENTION

In order to solve the problem that there are fewer kinds of catalysts for preparing dimethyl disulfide by catalytic oxidation of methanthiol in the art, the present invention provides a catalyst for oxidization of methanthiol which has a high catalytic conversion rate, a low cost and is suitable for industrial production, and also provides methods for preparation and application.

In one aspect, the present invention provides a new use of magnetic iron oxide red $Fe_{21.333}O_{32}$ as a catalyst in a method for preparing dimethyl disulfide by oxidization of methanthiol.

In a class of embodiments, the catalyst consists of magnetic iron oxide red $Fe_{21.333}O_{32}$ in an amount of 80-95 wt %, and the balance is a binder.

In another aspect, the present invention provides a method for preparing the catalyst, comprising:

(1) preparing a solution of a soluble carbonate and a soluble ferrous salt by controlling a molar ratio of the carbonate to the ferrous salt to 1:0.8-1.5, stirring the solution to allow the carbonate reacting with the ferrous salt in the solution to form a first mixture, and filtrating the first mixture to obtain a filter cake;

(2) calcining the filter cake at 250-400° C. for 2-5 h, then washing with water and drying the filter cake to yield the magnetic iron oxide red $Fe_{21.333}O_{32}$;

(3) mixing the magnetic iron oxide red $Fe_{21.333}O_{32}$ obtained in step (2) and a binder to form a second mixture, followed by roll molding at room temperature and drying the second mixture to produce the catalyst.

In a class of embodiments, the soluble carbonate is sodium carbonate or potassium carbonate, and the soluble ferrous salt is ferrous sulfate.

In a class of embodiments, the ferrous sulfate has a concentration of 1.5-3.0 mol/L in the solution.

In a class of embodiments, the ferrous sulfate has a concentration of 2.2 mol/L in the solution.

In a class of embodiments, calcining the filter cake at 300° C. in the step (2).

In a class of embodiments, the binder is polyvinyl alcohol or red clay.

In a class of embodiments, drying the second mixture at a temperature no more than 100° C. in the step (3).

In a further aspect, the present invention provides a method for preparing dimethyl disulfide by catalytic oxidation of methanthiol using the catalyst of the present invention, comprising, introducing a gas mixture of a methanthiol gas and an oxygen containing gas, wherein a molar ratio of the oxygen in the oxygen containing gas and the methanthiol gas is equal to or more then 1:3, into a fixed bed reactor for reacting in the presence of the catalyst by controlling a reaction temperature to 10-150° C., an space velocity of the gas mixture to 500-2000 $h^{-1}$, and a reaction pressure to atmospheric pressure.

In the method for preparing the catalyst for preparing dimethyl disulfide by oxidization of methanthiol of the present invention, the step (1) comprises preparing a solution of a soluble carbonate and a soluble ferrous salt by controlling a molar ratio of the carbonate to the ferrous salt to 1:0.8-1.5, stirring the solution to allow the carbonate reacting with the ferrous salt in the solution to form a first mixture, and filtrating the first mixture to obtain a filter cake. By specially controlling the molar ratio of the carbonate to the ferrous salt to 1:0.8-1.5, the used raw materials can react sufficiently and thus the yield of magnetic iron oxide red is high, and in addition the used raw materials are low in cost. The step (2) comprises calcining the filter cake obtained in the step (1) at 250-400° C. for 2-5 h, then washing with water and drying the filter cake to yield the magnetic iron oxide red $Fe_{21.333}O_{32}$. The step (3) comprises mixing the magnetic iron oxide red $Fe_{21.333}O_{32}$ obtained in step (2) and a binder to form a second mixture, followed by roll molding at room temperature and drying the second mixture to produce the catalyst. In a preferred embodiment, the present invention employs polyvinyl alcohol or red clay as the binder, which can impart the catalyst a high mechanical strength, and can benefit the molding operation.

The present invention has the following advantages:

Under a circumstance that there lacks of intensive study on catalyst for catalytic oxidation of methanthiol in the prior art, the inventors of the present invention carried out a lot of long-term researches and surprisingly found that when the magnetic iron oxide red $Fe_{21.333}O_{32}$ prepared by inventors themselves is used as the catalyst for preparing dimethyl disulfide by oxidization of methanthiol, a very high catalytic conversion rate can be achieved. In addition, since the magnetic iron oxide red $Fe_{21.333}O_{32}$ is prepared using carbonates and ferrous salts as raw materials, the present invention has advantages of low cost and simple preparation technology, and is very suitable for industrial production.

DESCRIPTION OF EMBODIMENTS

Example 1

Figure 1:
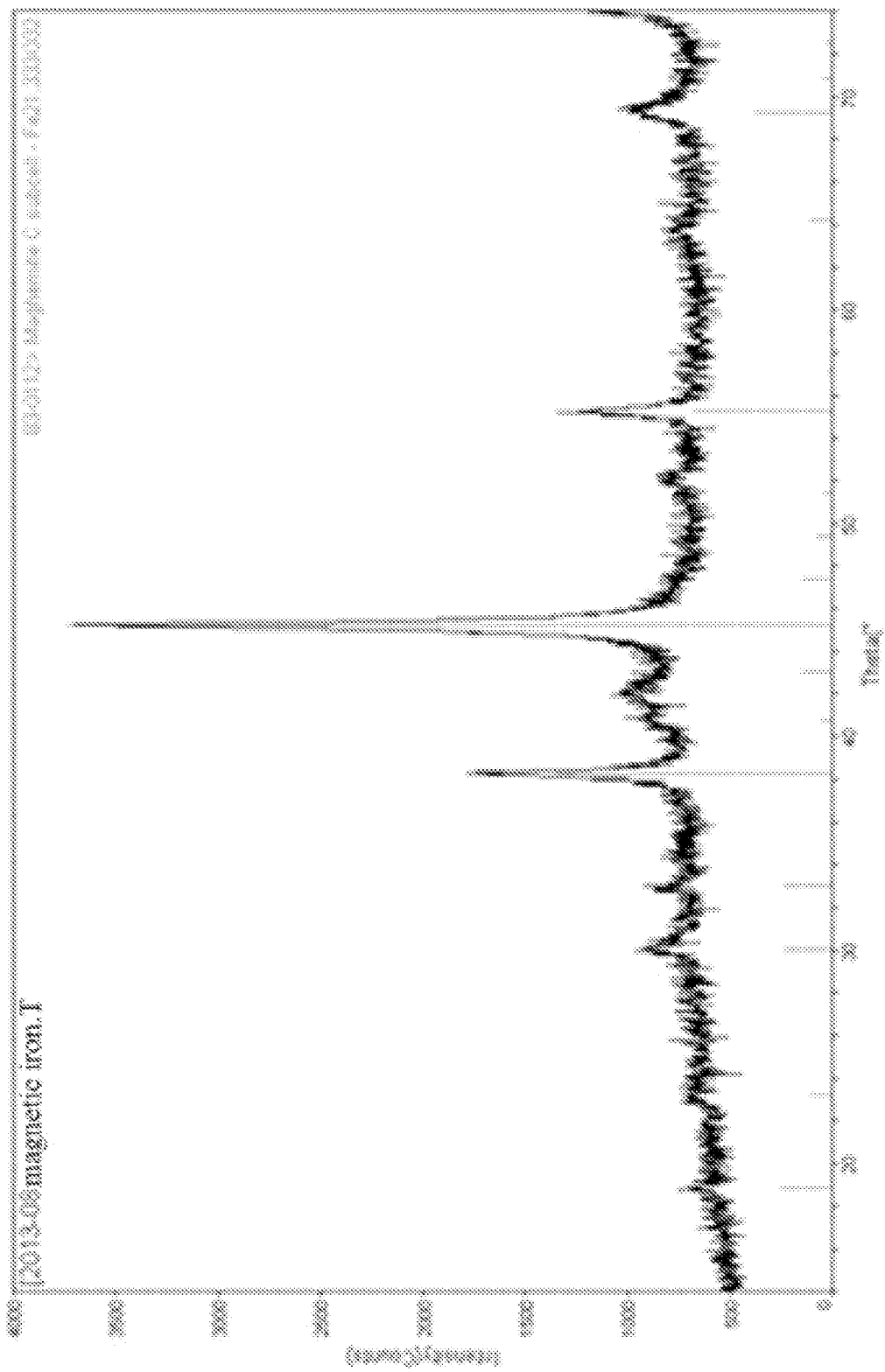
FIG. 1 shows a XRD pattern of the magnetic iron oxide red $Fe_{21.333}O_{32}$ prepared in the present invention.

A method for preparing a catalyst for oxidization of methanthiol in the present example comprises:

(1) adding water into a beaker, placing the beaker in a water bath at 40° C., putting $FeSO_4.7H_2O$ solid into the beaker, followed by stirring until the $FeSO_4.7H_2O$ solid is completely dissolved in the water to obtain a $FeSO_4$ solution having a concentration of 1.5 mol/L; then slowly adding $Na_2CO_3$ solid into the $FeSO_4$ solution by controlling a molar ratio of the $Na_2CO_3$ to the $FeSO_4$ to 1 to form a first mixture; stirring the first mixture for 2 h, followed by suction filtration to obtain a filter cake;

(2) putting the filter cake prepared by step (1) into a muffle furnace, calcining the filter cake at 300° C. for 3 h, then washing with water and filtering for 3 times, followed by drying the filter cake at 100° C. to yield the magnetic iron oxide red $Fe_{21.333}O_{32}$; and (3) mixing 80 g of the magnetic iron oxide red $Fe_{21.333}O_{32}$ obtained in step (2) with 80 g of polyvinyl alcohol as a binder to form a second mixture, followed by roll molding at room temperature and drying the second mixture at room temperature to produce the catalyst A.

The catalyst in the present example consists of magnetic iron oxide red $Fe_{21.333}O_{32}$ in an amount of 80 wt %, and the balance is the binder.

Example 2

(1) Adding water into a beaker, placing the beaker in a water bath at 40° C., putting $FeSO_4.7H_2O$ solid into the beaker, followed by stirring until the $FeSO_4.7H_2O$ solid is completely dissolved in the water to obtain a $FeSO_4$ solution having a concentration of 3 mol/L; then slowly adding $Na_2CO_3$ solid into the $FeSO_4$ solution by controlling a molar ratio of the $Na_2CO_3$ to the $FeSO_4$ to 0.8 to form a first mixture; stirring the first mixture for 2 h, followed by suction filtration to obtain a filter cake;

(2) putting the filter cake prepared by step (1) into a muffle furnace, calcining the filter cake at 300° C. for 3 h, then washing with water and filtering for 3 times, followed by drying the filter cake at 120° C. to yield the magnetic iron oxide red $Fe_{21.333}O_{32}$; and (3) mixing 85 g of the magnetic iron oxide red $Fe_{21.333}O_{32}$ obtained in step (2) with 15 g of red clay as a binder to form a second mixture, followed by roll molding at room temperature and drying the second mixture at 90° C. to produce the catalyst B.

The catalyst of the present example consists of magnetic iron oxide red $Fe_{21.333}O_{32}$ in an amount of 85 wt %, and the balance is the binder.

Example 3

(1) Adding water into a beaker, placing the beaker in a water bath at 40° C., putting $FeSO_4.7H_2O$ solid into the beaker, followed by stirring until the $FeSO_4.7H_2O$ solid is completely dissolved in the water to obtain a $FeSO_4$ solution having a concentration of 2.2 mol/L; then slowly adding $Na_2CO_3$ solid into the $FeSO_4$ solution by controlling a molar ratio of the $Na_2CO_3$ to the $FeSO_4$ to 1.5 to form a first mixture; stirring the first mixture for 2 h, followed by suction filtration to obtain a filter cake;

(2) putting the filter cake prepared by step (1) into a muffle furnace, calcining the filter cake at 300° C. for 3 h, then washing with water and filtering for 3 times, followed by drying the filter cake at 190° C. to yield the magnetic iron oxide red $Fe_{21.333}O_{32}$; and (3) mixing 85 g of the magnetic iron oxide red $Fe_{21.333}O_{32}$ obtained in step (2) with 15 g of polyving akohol as a binder to form a second mixture, followed by roll molding at room temperature and drying the second mixture at 90° C. to produce the catalyst C.

The catalyst of the present example consists of magnetic iron oxide red $Fe_{21.333}O_{32}$ in an amount of 85 wt %, and the balance is the binder.

FIG. 1 shows the XRD pattern of the magnetic iron oxide red $Fe_{21.333}O_{32}$ prepared by the above examples.

Test Example

In order to demonstrate the catalytic effect of the magnetic iron oxide red $Fe_{21.333}O_{32}$ for oxidization of methanthiol, the present invention provides the test example to evaluate the performance of the catalysts.

The evaluation test is performed in a quartz fixed bed reactor of Ø10 mm×100 mm, filled with the catalyst to reach a height of 40 mm. A gas mixture of methanthiol gas and an oxygen with a molar ratio of 3:1-5:1 is introduced into the quartz fixed bed reactor under the condition of a reaction temperature of 10-100° C., a space velocity of 500-2000 $h^{-1}$, and a reaction pressure of atmospheric pressure. The specific parameter settings are listed in the following table.

The catalytic conversion rate X of the catalyst of each example is calculated according to the formula below:

$$X = \text{dimethyl disulfide}_{actual\ output} / \text{dimethyl disulfide}_{theoretical\ output} \times 100\%$$

wherein dimethyl disulfide theoretical output is calculated according to the methanthiol introduced into the fixed bed reactor.

Figure 2:
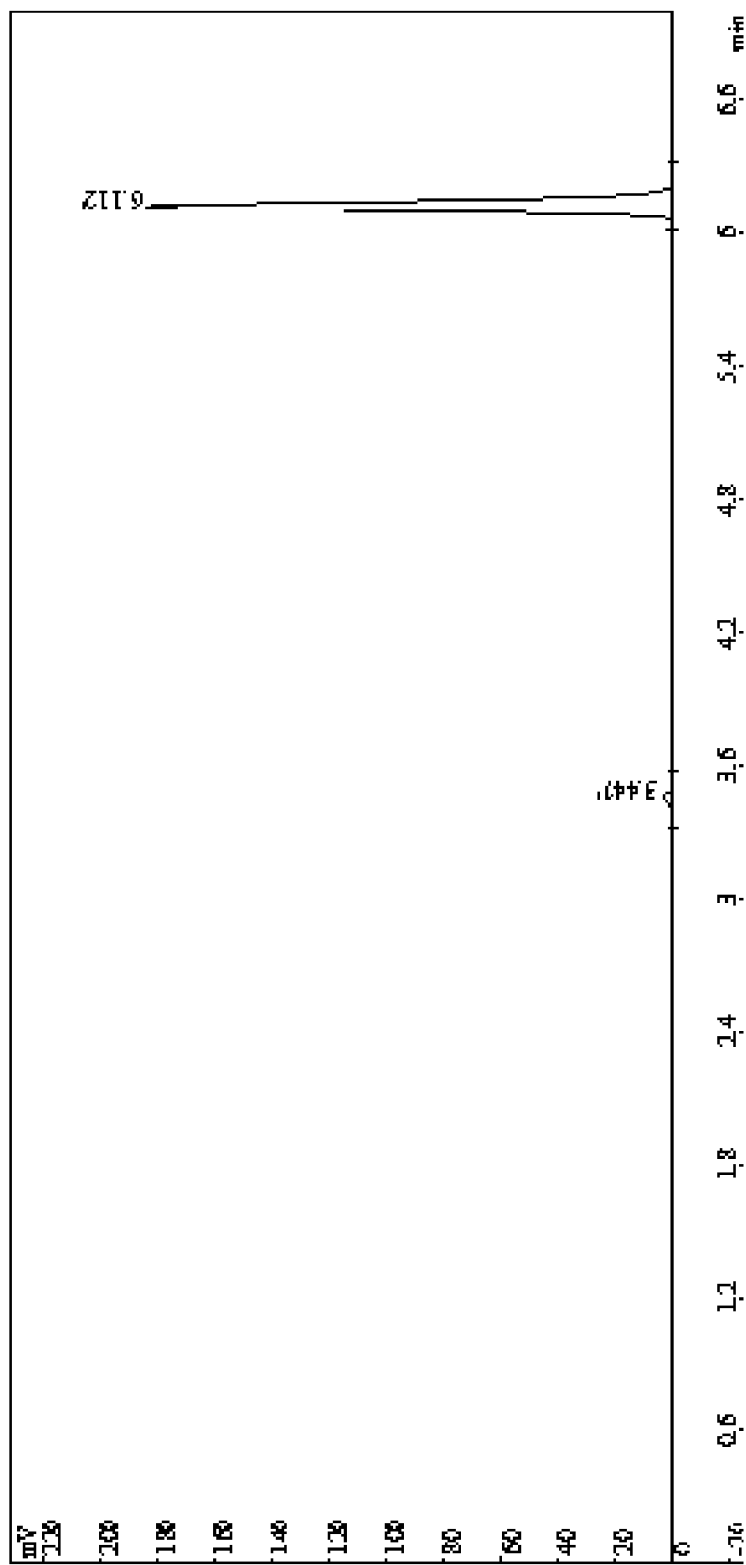
FIG. 2 shows a gas chromatogram of $CH_3SSCH_3$ standard sample.
Figure 3:
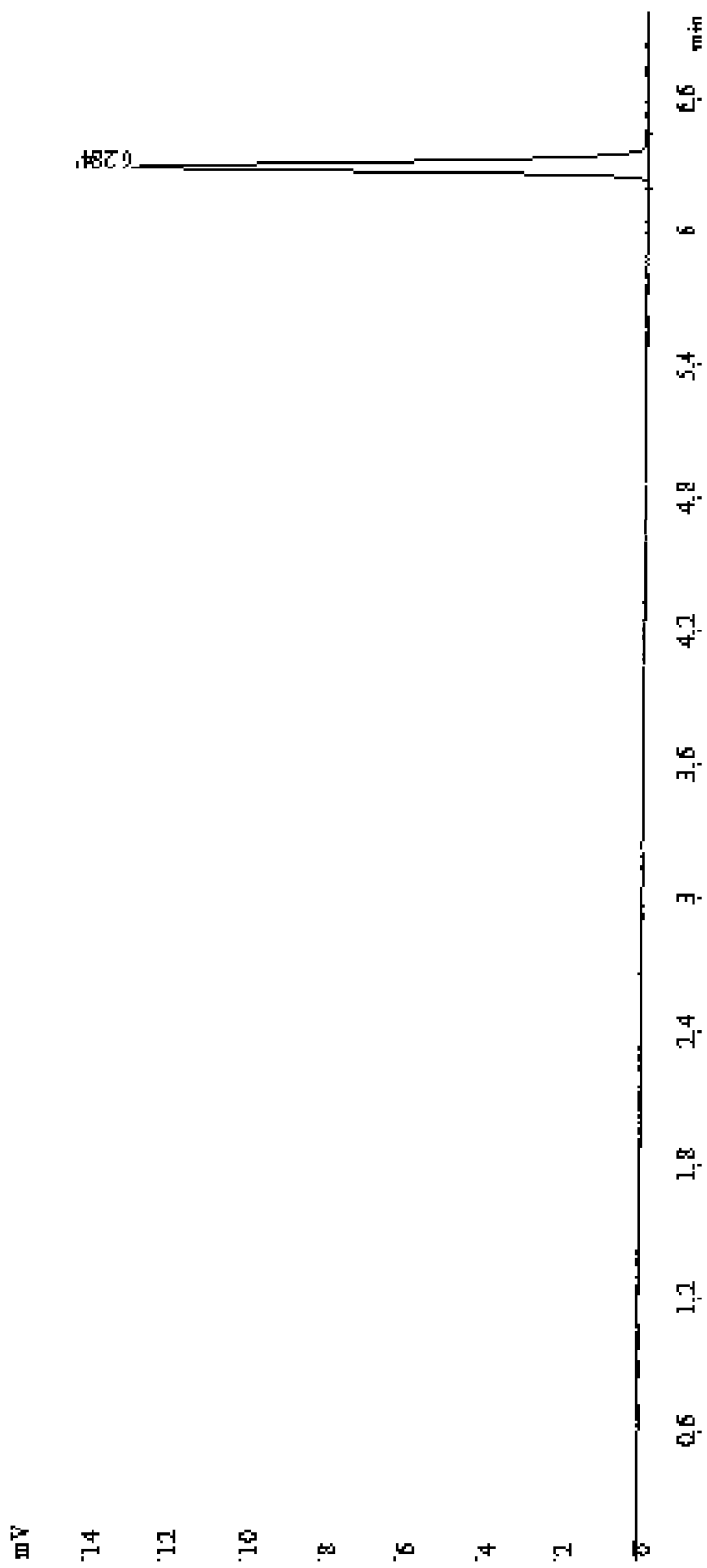
FIG. 3 shows a gas chromatogram of outlet gas sample.

In the present example, gas chromatograph is used for qualitative and quantitative detection of the dimethyl disulfide in the products. The chromatograms of the standard sample and outlet gas sample of the dimethyl disulfide are shown in FIGS. 2 and 3. According to the chromatogram, under same conditions, the peak appearance time of the $CH_3SSCH_3$ standard sample is almost the same with that of the sulfur containing compound in the outlet gas sample, so it can be determined that the sulfur containing compound in the outlet gas is $CH_3SSCH_3$.

After detection, the catalytic conversion rates of the catalysts of examples 1-3 are summarized in the table below:

| Catalyst | reaction temperature °C. 10 | gas space velocity h⁻¹ 500 | molar ratio 3:1 | reaction temperature °C. 25 | gas space velocity h⁻¹ 1000 | molar ratio 4:1 | reaction temperature °C. 70 | gas space velocity h⁻¹⁻¹ 2000 | molar ratio 4:1 | reaction temperature °C. 100 | gas space velocity h⁻¹ 700 | molar ratio 5:1 |
|---|---|---|---|---|---|---|---|---|---|---|---|---|
| Catalyst A | 92.1% | | | 93.3% | | | 90.6% | | | 94.9% | | |
| Catalyst B | 91.9% | | | 92.6% | | | 90.2% | | | 88.7% | | |
| Catalyst C | 96.4% | | | 96.8% | | | 93.7% | | | 95.2% | | |

From the above results it is known that the magnetic iron oxide red $Fe_{21.333}O_{32}$ has an excellent catalytic oxidation effect when used as a catalyst for oxidization of methanthiol.

Obviously, the above embodiments are merely examples for clear illustration, rather than limitation for the application. For those skilled in the art, changes and modifications may be made on the basis of the above description, and it is not necessary and could not exhaust all embodiments, thus obvious changes and modifications derived from the above embodiments still fall within the protection scope of the invention.

The invention claimed is:

1. A method for preparing dimethyl disulfide, wherein the method comprises oxidizing methanthiol in presence of a catalyst comprising magnetic iron oxide red ($Fe_{21.333}O_{32}$).

2. The method of claim 1, wherein the catalyst consists of magnetic iron oxide red ($Fe_{21.333}O_{32}$) in an amount of 80-95 wt %, and a binder.

3. The method of claim 1, wherein the catalyst is prepared by a method comprising:
   preparing a solution of a soluble carbonate and a soluble ferrous salt by providing the solution in a controlled molar ratio of the carbonate to the ferrous salt of 1:0.8-1.5, stirring the solution to allow the carbonate to react with the ferrous salt in the solution to form a first mixture, and filtrating the first mixture to obtain a filter cake;
   calcining the filter cake at a temperature of 250-400° C. for two to five hours, then washing with water and drying the filter cake to yield the magnetic iron oxide red ($Fe_{21.333}O_{32}$); and
   mixing the magnetic iron oxide red ($Fe_{21.333}O_{32}$) and a binder to form a second mixture, followed by roll molding at room temperature and drying the second mixture to produce the catalyst.

4. The method of claim 3, wherein the soluble carbonate is sodium carbonate or potassium carbonate, and the soluble ferrous salt is ferrous sulfate.

5. The method of claim 4, wherein the ferrous sulfate has a concentration of 1.5-3.0 mol/L in the solution.

6. The method of claim 4, wherein the ferrous sulfate has a concentration of 2.2 mol/L in the solution.

7. The method of claim 3, wherein calcining the filter cake is at a temperature of 300° C.

8. The method of claim 3, wherein the binder is polyvinyl alcohol or red clay.

9. The method of claim 3, wherein drying the second mixture is at a temperature of no more than 100° C.

10. The method of claim 1, wherein the method comprises,
    introducing a gas mixture of a methanthiol gas and an oxygen containing gas into a fixed bed reactor, reacting the gas mixture in the presence of catalyst under controlled conditions of a reaction temperature of 10-150° C., a space velocity of the gas mixture of 500-2000 h⁻¹, and a reaction pressure of atmospheric pressure, wherein a molar ratio of the oxygen in the oxygen containing gas and the methanthiol gas is equal to or greater than 1:3.

11. The method of claim 10, wherein the catalyst is prepared by a method comprising:
    preparing a solution of a soluble carbonate and a soluble ferrous salt by providing the solution in a controlled molar ratio of the carbonate to the ferrous salt of 1:0.8-1.5, stirring the solution to allow the carbonate to react with the ferrous salt in the solution to form a first mixture, and filtrating the first mixture to obtain a filter cake;
    calcining the filter cake at 250-400° C. for two to five hours, then washing with water and drying the filter cake to yield the magnetic iron oxide red ($Fe_{21.333}O_{32}$); and
    mixing the magnetic iron oxide red $Fe_{21.333}O_{32}$ and a binder to form a second mixture, followed by roll molding at room temperature, and drying the second mixture to produce the catalyst.

12. The method of claim 11, wherein the catalyst consists of magnetic iron oxide red $Fe_{21.333}O_{32}$ in an amount of 80-95 wt %, and a binder.

* * * * *